United States Patent [19]

Gold et al.

[11] 4,340,597

[45] Jul. 20, 1982

[54] 1-SUBSTITUTED-4-ARYL-1,2,5,6-TETRAHYDRO AND HEXAHYDROPYRIDINES

[75] Inventors: Elijah H. Gold, West Orange; Joel G. Berger, Verona; Wei K. Chang, Livingston, all of N.J.

[73] Assignee: Schering Corporation, Kenilworth, N.J.

[21] Appl. No.: 253,137

[22] Filed: Apr. 13, 1981

[51] Int. Cl.$^3$ ................. C07D 471/04; A61K 31/435
[52] U.S. Cl. .................................. 424/256; 424/263; 546/119; 546/271
[58] Field of Search ................ 546/119, 271; 424/256, 424/263

[56] References Cited

U.S. PATENT DOCUMENTS 3,381,009  4/1968  Palazzo et al. ...................... 544/127
4,251,530  2/1981  Saari et al. .......................... 546/120

OTHER PUBLICATIONS

Baiocchi et al., Chem. Abst. 81-105409r, 1974.
Chem. Abst. 1448552, vol. 76, 1972.

Primary Examiner—Jane T. Fan
Attorney, Agent, or Firm—Gerald S. Rosen; Bruce M. Eisen

[57] ABSTRACT

Disclosed herein are certain 1-substituted-4-aryl-1,2,5,6-tetrahydro and hexahydro triazolo pyridines which are useful as analgesics.

20 Claims, No Drawings

1-SUBSTITUTED-4-ARYL-1,2,5,6-TETRAHYDRO AND HEXAHYDROPYRIDINES

The invention relates to certain 1-substituted-4-aryl-1,2,5,6-tetrahydro and hexahydropyridines, to their pharmaceutically acceptable acid addition salts, to methods for their preparation and to methods for their use as analgesics. This invention also relates to pharmaceutical compositions and processes for the production thereof.

The compounds of this invention may be depicted by the following formula:

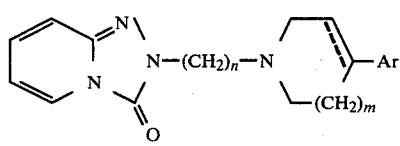

I and to pharmaceutically acceptable acid addition salts thereof and to pharmaceutical compositions containing them wherein Ar is phenyl or phenyl substituted by one or more members of the group consisting of halogeno, ($C_1$–$C_5$) lower alkyl, halogeno lower alkyl, hydroxyl, and ($C_1$–$C_5$) lower alkoxyl; m is an integer of zero or 1, n is an integer of 2 or 3; and the dotted line represents an optional double bond.

PRIOR ART

Palazzo et al. disclosed in U.S. Pat. No. 3,381,009 compounds of the formula:

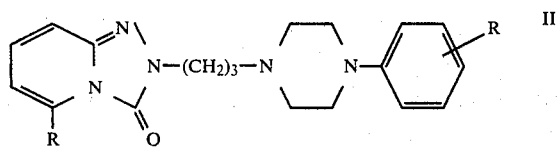

II wherein R is hydrogen or methyl, R' is lower alkyl, alkoxy or halogen. The compounds are useful as tranquilizers, hypotensives and analgesics.

The novel compounds of this invention may be prepared by one or more of the following reaction sequences.

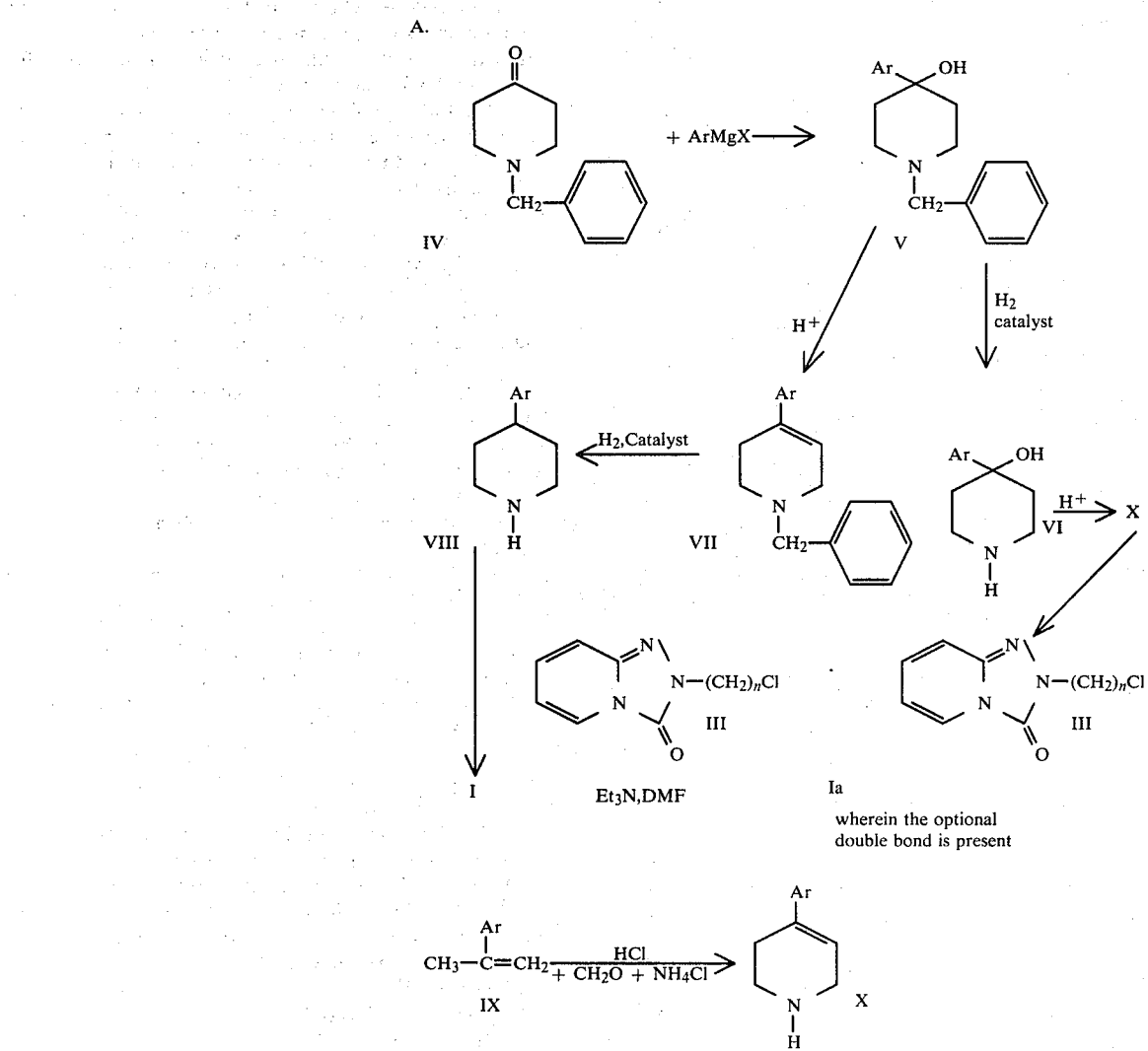

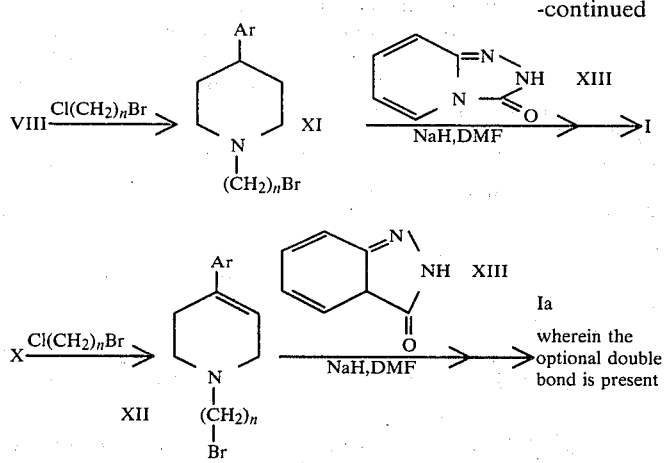

In reaction Sequence A, N-benzyl-4-piperidone IV is reacted with an aryl Grignard reagent in an ether, such as tetrahydrofuran or diethyl ether. The resulting compound V is then debenzylated with hydrogen gas over a metal catalyst such as palladium on carbon, palladium hydroxide, or Raney nickel in an alcoholic solvent at 1 to 5 atmospheres pressure. The resulting product VI is treated with a strong mineral acid (e.g. hydrochloric or sulfuric acids) in an alcohol to yield compound X. Compound X may also be prepared by reacting an appropriately substituted α-methyl styrene IX with ammonium chloride and formaldehyde under acidic conditions as described by Janssen in Belgian Pat. No. 577,977 (published May 15, 1959).

Compounds VIII may be prepared by dehydration of compounds V with mineral acid to give compounds VII which can then be treated with hydrogen and a noble metal catalyst e.g. Pd/c in an alcoholic medium to give compounds X. Treatment of VI or X with III in the presence of a tertiary amine base e.g. triethylamine, gives compounds I and Ia, respectively. Compound III may be prepared as described by Palazzo and Silvestrini in U.S. Pat. No. 3,381,009.

In reaction Sequence B, VIII or X is treated with α,ω-chlorobromoalkane in a suitable solvent as described by Pelz and Protiva, *Coll. Czech. Chem. Comm.*, 32, 2840 (1967) and the resulting XI or XII is used to alkylate the salt of commercially available XIII. The alkylation is effected in a polar non-aqueous solvent (e.g. dimethylformamide) containing an alkali metal hydride (e.g. sodium hydride) to yield I and Ia, respectively.

The following examples are illustrative of the above reaction Sequences for the preparation of the compounds of this invention.

EXAMPLE I

2-[3-[1-(1,2,5,6-Tetrahydro-4-(2-methylphenyl)-pyridinyl)]Propyl]-1,2,4-Triazolo[4,3-a]pyridin-3(2H)-one (A) 1-Benzyl-4-hydroxy-4-(2-methylphenyl)piperidine hydrochloride To a Grignard reagent prepared from 5.3 g of magnesium turnings and 37 g of 1-bromo-2-methyl benzene in 150 ml of dry tetrahydrofuran add dropwise with stirring 19.0 g of 1-benzyl-4-piperidone while maintaining the temperature at −10° to −20° C. Allow the reaction mixture to warm to ambient temperature and stir overnight. Cool the reaction mixture to 10° C. and decompose the reaction mixture with 20% hydrochloric acid (100 mls). Add ethyl ether to form a two-phase system from which a solid precipitates. Filter, wash the precipitate with saturated sodium chloride, then with ethyl ether and dry *in vacuo*. M.P. 181°–183° C.

Convert the precipitate to the free base with 10% sodium hydroxide. Extract with ethyl ether, treat the ethereal solution with hydrogen chloride in ether to yield the hydrochloride salt as a crystalline precipitate. Recrystallize the product from acetonitrile to obtain thereby the product of this step. M.P. 215°–216° C.

(B) 4-Hydroxy-4-(2-methylphenyl)piperidine

Convert 25 g of the product of step A to the free base with 10% aq naoh and ethyl ether. Separate the ethereal solution and concentrate to an oil weighing 18.3 g. Dissolve the oil in 200 ml of absolute ethanol and hydrogenate over 4 g of 20% palladium hydroxide on carbon at 60 psig. Remove the catalyst by filtration and concentrate the filtrate to a solid. Recrystallize the product from ethyl acetate to obtain thereby the product of this step, M.P. 138°–140° C.

(C) 4-(2-methylphenyl-1,2,5,6-tetrahydro)pyridine hydrochloride

Dissolve 2.7 g of the product of step B in 20 ml of concentrated hydrochloric acid plus 20 ml of methanol and reflux for three hours. Concentrate the solution to a gummy residue and dry by azeotroping with benzene. Triturate the solid which forms during the azeotroping process with ethyl ether, filter, wash with ethyl ether and dry. M.P. 236°–239° C.

(D) 2-[3-[1-(1,2,5,6-Tetrahydro)-(2-methylphenyl)-pyridinyl)]-propyl]-1,2,4-triazolo[4,3-a]pyridin-3-(2H)-one Stir and heat on a steam bath for three hours a mixture of 2.3 g of the product from step C, 2.5 g of 2-(3-chloropropyl)-5-triazolo-[4,3-a]pyridine-3-one, powdered potassium iodide 0.5 g, triethyl amine 5.0 ml and dimethyl-formamide 20 ml. Pour the reaction mixture into water into water and filter. Dissolve the reddish precipitate in ethyl ether, dry over potassium carbonate, decolorize with activated charcoal and filter. Dilute the ethereal solution (100 ml) with 50 ml of hexane and concentrate to 75 ml, cool, and collect the product by filtration. M.P. 106°–107° C.

EXAMPLE 2

2-[3-[1-(4-Phenylpiperidino)-propyl]-1,2,4-triazolo[4,3-a]-Pyridine-3-(2H)one

Dissolve 5.12 g of 4-phenylpiperidine, 4.5 g of sodium iodide, 9.0 g of sodium carbonate (anhydrous) and 7.0 g of 2-(3-chloropropyl)-S-triazolo-[4,3-b]pyridine-3-one (prepared as described in U.S. Pat. No. 3,381,009) in 150 ml of dimethylformamide and heat in an oil bath at 100°-110° C. for four hours. Distill off the solvent *in vacuo.* Stir the residue with 100 ml of water with external cooling. Filter and wash with about 20 ml of cold water. Dissolve the solid product in 200 ml of boiling ethyl ether and cool to room temperature. Dry the ethereal solution over anhydrous potassium carbonate, filter and allow the ether to evaporate overnight. Filter the solid product, wash with cold ether and dry.

Dissolve the product in ethyl ether (250 ml), filter, concentrate to about 100 ml and chill. Filter the product to obtain thereby the product of this example. M.P. 102°-103° C.

Dissolve 20.4 g 1,2,4-triazolo-[4,3-a]-pyridine-3-one in 150 ml of dimethylformamide and heat with stirring to 90° C. Add 7.2 g of sodium hydride dispersion (50% NaH) in small portions and heat for an additional 10 minutes. Add a solution of 1-(3-chloropropyl)-4-phenyl piperidine (35 g) in 50 ml of dimethylformamide dropwise over a 15 minute interval. Stir the reaction mixture on a steam bath for 1½ hours, cool and concentrate *in vacuo.* Pour the residue into 500 ml of water with stirring, filter the crystalline suspension, wash with water and dry.

Recrystallize by dissolving in 500 ml of isopropyl ether-tetrahydrofuran and ethyl ether to obtain thereby the product of this example, M.P. 103.5° C. Concentrate the mother liquors to 150 ml to obtain additional product, M.P. 102°-104° C.

By substituting an equivalent quantity of other 4-hydroxy-4-phenyl-substituted piperidines or a 2 or 3-hydroxy-2 or 3-phenyl substituted pyrrolidine, wherein the phenyl moiety bears one or more of the following substituents halogen, lower alkyl, halo lower alkyl, hydroxyl or lower alkoxyl; and by following the processes of the preceding examples other phenyl substituted cyclic amino 4-triazolo pyridine 3-ones may be produced. Exemplary of such compounds are the following:

2-[3-(1-(4-p-CHLOROPHENYL-1,2,5,6-TETRAHYDROPYRIDYL))-PROPYL]1,2,4-TRIAZOLO[4,3-a]PYRIDIN-3(2H)-ONE

2-[3-[1-(1,2,5,6-TETRAHYDRO-4-(4-METHYLPHENYL)-PYRIDINYL)]-PROPYL]-1,2,4-TRIAZOLO[4,3-a]PYRIDIN-3(2H)-ONE

2-[3-[1-(4-(4-CHLOROPHENYL)-PIPERIDINYL)]-PROPYL]-1,2,4-TRIAZOLO[4,3-a]PYRIDIN-3(2H)-ONE

2-[3-[1-(4-(3-CHLOROPHENYL)-PIPERIDINYL)]-PROPYL]1,2,4-TRIAZOLO[4,3-a]PYRIDINE-3-(2H)-ONE

2-[3-[1-(4-(4-METHYLPHENYL)-PIPERIDINYL)]-PROPYL]-1,2,4-TRIAZOLO-[4,3-a]PYRIDINE-3-(2H)-ONE

2-[3-[1-(4-(3-METHYLPHENYL)-PIPERIDINYL)]-PROPYL]-1,2,4-TRIAZOLO[4,3-a]PYRIDINE-3-(2H)-ONE

2-[3-[1-(1,2,5,6-TETRAHYDRO)-4-(3-CHLOROPHENYL)-PYRIDINYL]-PROPYL]-1,2,4-TRIAZOLO[4,3-a]PYRIDIN-3-(2H)-ONE

2-[3-[1-(4-(4-FLUOROPHENYL)-PIPERIDINYL)]-PROPYL]1,2,4-TRIAZOLO-[4,3-a]PYRIDIN-3(2H)-ONE

2-[3-[1-(4-PHENYLPIPERIDINO)-PROPYL]-1,2,4-TRIAZOLO[4,3-a]]-PYRIDIN-3(2H)ONE

2-[3-[1-(1,2,5,6-TETRAHYDRO-4-(2-METHYLPHENYL)-PYRIDINYL)]-PROPYL]-1,2,4-TRIAZOLO[4,3-a]PYRIDIN-3(2H)-ONE

2-[3-[1-(4-(4-METHOXYPHENYL)-PIPERIDINO)]-PROPYL]-1,2,4-TRIAZOLO[4,3-a]PYRIDIN-3(2H)-ONE

2-[3-[1-(3-PHENYLPYRROLIDINYL)]-PROPYL]-1,2,4-TRIAZOLO[4,3-a]-PYRIDINE-3-(2H)-ONE

2-[3-[1-(1,2,5,6-TETRAHYDRO)-4-(2-TRIFLUOROMETHYLPHENYL)-PYRIDINYL]-PROPYL]-1,2,4-TRIAZOLO[4,3-a]PYRIDIN-3(2H)-One

2-[3-[1-(4-(3-HYDROXYPHENYL)-PIPERIDINO)]-PROPYL]-1,2,4-TRIAZOLO[4,3-a]PYRIDIN-3(2H)-ONE

The compounds of this invention elicit an analgesic effect upon administration to warm-blooded animals suffering from pain. In conventional tests such as the mouse writhing and the rat yeast paw the compounds of this invention substantially reduced the pain associated with these test and had favorable $ED_{50}$s in the mouse writhing tests. Advantageously, the compounds of this invention exhibit essentially no hypotensive or tranquilizing properties as do many analgesics known in the art.

In most inventions involving pharmacological activity some members of the genus are more preferred than others. In some instances the preference is based upon economic considerations such, as the cost of the starting materials or the ease or difficulty of the synthetic pathways. Still others are based upon the degree to which the compounds elicit the desired effect at a given dosage level.

The preferred compounds of this invention are the first ten compounds set forth hereinabove. A most preferred pair of compounds of this group are 2-[-3(-1-4-phenylpiperidino)-propyl]-1,2,4-triazolo[4,3-a]pyridine-3(2H) one and 2-[3-[1-(1,2,5,6-tetrahydro-4-(2-methylphenyl)-pyridinyl)]-propyl]-1,2,4-triazolo[4,3-a]pyridin-3(2H)-one.

On the basis of the aforementioned tests and particularly in view of their $ED_{50}$ values in the mouse writhing test which range from about 1.2 mpk to about 5.5 mpk these compounds may be administered at from about 50 to about 300 mg/kg/day in divided doses administered about 3 to 4 times a day. However, the dose given and the frequency of the doses depend upon the general physical condition of the patient, the age of the patient, the cause and degree of the pain, if known and, therefore, must be left to the skilled health provided.

The compounds of this invention are nitrogen bases and may be administered as the free base, or may be administered in form of an acid addition salt of an inorganic or an organic acid. The acids contemplated are those generally used in pharmaceutical products, i.e. the pharmaceutically acceptable acids. In whatever form the compounds are administered, they may be compounded with the binders, fillers or other excipients generally used in the art. They may be compounded as tablets, capsules or elixirs for oral administration and in solutions and suspensions for parenteral administration.

We claim:
1. A compound of the formula

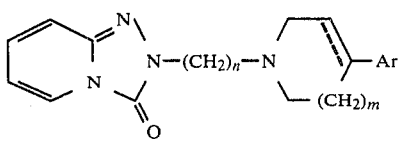

or a pharmaceutically acceptable acid addition salt thereof wherein Ar is phenyl or phenyl substituted by one or more members of the group consisting of halogeno, ($C_1$–$C_5$) lower alkyl, halogeno lower alkyl, hydroxyl and ($C_1$–$C_5$) lower alkoxyl; m is an integer of zero or 1, n is an integer of 2 or 3; and the dotted line represents an optional double bond.

2. A compound of claim 1 of the formula:

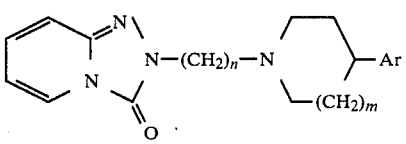

wherein Ar, m and n are as defined in claim 1.

3. A compound of claim 1 of the formula:

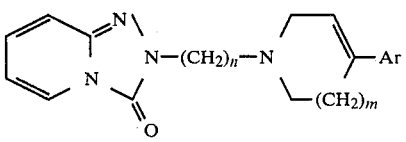

wherein Ar, m and n are as defined in claim 1.

4. A compound of claim 1 of the group consisting of the following:
2-[3-(1-(4-p-CHLOROPHENYL-1,2,5,6-TETRAHYDROPYRIDYL))-PROPYL]1,2,4-TRIAZOLO[4,3-a]PYRIDIN-3(2H)-ONE;
2-[3-[1(1,2,5,6-TETRAHYDRO-4-(4-METHYLPHENYL)-PYRIDINYL)]-PROPYL]-1,2,4-TRIAZOLO[4,3-a]PYRIDIN-3(2H)-ONE;
2-[3-[1-(4-(4-CHLOROPHENYL)-PIPERIDINYL)]-PROPYL]-1,2,4-TRIAZOLO[4,3-a]PYRIDIN -3(2H)-ONE;
2-[3-[1-(4-(3-CHLOROPHENYL)-PIPERIDINYL)]-PROPYL]1,2,4-TRIAZOLO[4,3-a]PYRIDINE-3-(2H)-ONE;
2-[3-[1-(4-(4-METHYLPHENYL)-PIPERIDINYL)]-PROPYL]1,2,4-TRIAZOLO-[4,3-a]PYRIDINE-3-(2H)-ONE;
2-[3-[1-(4-(3-METHYLPHENYL)-PIPERIDINYL)]-PROPYL]-1,2,4-TRIAZOLO[4,3-a]PYRIDINE-3-(2H)-ONE;
2-[3-[1-(1,2,5,6-tetrahydro)-4-(3-CHLOROPHENYL)-PYRIDINY L]-PROPYL]-1,2,4-TRIAZOLO[4,3-a]PYRIDIN-3-(2H)-ONE;
2-[3-[1-(4-(4-FLUOROPHENYL)-PIPERIDINYL)]-PROPYL]1,2,4-TRIAZOLO-[4,3-a]PYRIDIN-3(2H)-ONE;
2-[3-[1-(4-PHENYLPIPERIDINO)-PROPYL]-1,2,4-TRIAZOLO[4,3-a]-PYRIDIN-3(2H)-ONE; and
2-[3-[1-(1,2,5,6-TETRAHYDRO-4-(2-METHYLPHENYL)-PYRIDINYL)]-PROPYL]-1,2,4-TRIAZOLO[4,3-a]PYRIDIN-3(2H)-ONE.

5. A compound of claim 4, said compound being 2-[3-(1-(4-p-CHLOROPHENYL-1,2,5,6-TETRAHYDROPYRIDYL))-PROPYL]1,2,4-TRIAZOLO[4,3-a]PYRIDIN-3(2H)-ONE.

6. A compound of claim 4, said compound being 2-[3-[1-(1,2,5,6-TETRAHYDRO-4-(4-METHYLPHENYL)-PYRIDINYL)]-PROPYL]-1,2,4-TRIAZOLO[4,3-a]PYRIDIN-3(2H)-ONE.

7. A compound of claim 4, said compound being 2-[3-[1-(4-(4-CHLOROPHENYL)-PIPERIDINYL)]-PROPYL]-1,2,4-TRIAZOLO[4,3-a]-PYRIDIN-3(2H)-ONE.

8. A compound of claim 4, said compound being 2-[3-[1-(4-(3-CHLOROPHENYL)-PIPERIDINYL)]-PROPYL]1,2,4-TRIAZOLO)[4,3-a]-PYRIDINE-3-(2H)-ONE.

9. A compound of claim 4, said compound being 2-[3-[1-(4-(4-METHYLPHENYL)-PIPERIDINYL)]-PROPYL]-1,2,4-TRIAZOLO-[4,3-a]-PYRIDINE-3-(2H)-ONE.

10. A compound of claim 4, said compound being 2-[3-[1-(4-(3-METHYLPHENYL)-PIPERIDINYL)]-PROPYL]-1,2,4-TRIAZOLO[4,3-a]-PYRIDINE-3-(2H)-ONE.

11. A compound of claim 4, said compound being 2-[3-[1-(1,2,5,6-TETRAHYDRO)-4-(3-CHLOROPHENYL)-PYRIDINYL]-PROPYL]-1,2,4-TRIAZOLO[4,3-a]PYRIDIN-3-(2H)-ONE.

12. A compound of claim 4, said compound being 2-[3-[1-(4-(4-FLUOROPHENYl)-PIPERIDINYL)]-PROPYL]1,2,4-TRIAZOLO-[4,3-a]-PYRIDIN-3(2H)-ONE.

13. A compound of claim 4, said compound being 2-[3-(1-(4-PHENYLPIPERIDINO))-PROPYL]-1,2,4-TRIAZOLO[4,3-a]-PYRIDIN-3-(2H)-ONE.

14. A compound of claim 4, said compound being 2-[3-[1-(1,2,5,6-TETRAHYDRO-4-(2-METHYLPHENYL)-PYRIDINYL)]-PROPYL]-1,2,4-TRIAZOLO[4,3-a]PYRIDIN-3(2H)-ONE.

15. A method of eliciting an analgesic response from a warm blooded animal suffering with pain which comprises administering to the animal an effective analgesic amount of a compound of the formula

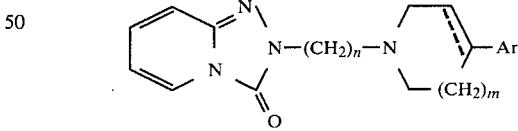

or a pharmaceutically acceptable acid addition salt thereof wherein Ar is phenyl or phenyl substituted by one or more members of the group consisting of halogeno, ($C_1$–$C_5$) lower alkyl, halogeno lower alkyl, hydroxyl and ($C_1$–$C_5$) lower alkoxyl; m is an integer of zero or 1, n is an integer of 2 or 3; and the dotted line represents an optional double bond.

16. A pharmaceutical composition for the treatment of pain comprising an effective analgesic amount of a compound of claim 1 and a pharmaceutically acceptable excipient.

17. The method of claim 15 wherein the compound administered is 2-[3-[1-(1,2,5,6-tetrahydro-4-(2-methylphenyl)-pyridinyl)]-propyl]-1,2,4-triazolo[4,3-a]pyridin-3(2H)-one.

18. The method of claim 15 wherein the compound administered is 2-[3-[1-(4-phenylpiperidino)-propyl]-1,2,4-triazolo[4,3-a]-pyridin-3-(2H)-one.

19. The pharmaceutical composition of claim 16 wherein said compound is 2-[3-[1-(1,2,5,6-tetrahydro-4-(2-methylphenyl)-pyridinyl)]-propyl]-1,2,4-triazolo[4,3-a]pyridin-3(2H)-one.

20. The pharmaceutical composition of claim 16 wherein said compound is 2-[3-[1-(4-phenylpiperidino)-propyl]-1,2,4-triazolo-[4,3-a]]-pyridin-3(2H)-one.

* * * * *